US009119565B2

(12) United States Patent
Levis et al.

(10) Patent No.: US 9,119,565 B2
(45) Date of Patent: Sep. 1, 2015

(54) INTRAOCULAR LENS ALIGNMENT

(75) Inventors: Ilias Levis, Westwood, MA (US); Katariina Lahti, Westwood, MA (US); Boris Nalibotski, New London, CT (US)

(73) Assignee: ALCON RESEARCH, LTD., Fort Worth, TX (US)

( * ) Notice: Subject to any disclaimer, the term of this patent is extended or adjusted under 35 U.S.C. 154(b) by 189 days.

(21) Appl. No.: 12/705,799

(22) Filed: Feb. 15, 2010

(65) Prior Publication Data
US 2010/0208199 A1    Aug. 19, 2010

Related U.S. Application Data

(60) Provisional application No. 61/153,709, filed on Feb. 19, 2009, provisional application No. 61/155,562, filed on Feb. 26, 2009.

(51) Int. Cl.
A61F 9/007 (2006.01)
A61B 3/11 (2006.01)
A61B 3/135 (2006.01)
A61F 9/00 (2006.01)
A61F 2/16 (2006.01)

(52) U.S. Cl.
CPC . A61B 3/11 (2013.01); A61B 3/135 (2013.01); A61F 2/16 (2013.01); A61F 9/007 (2013.01); A61F 9/0008 (2013.01); A61F 9/0017 (2013.01)

(58) Field of Classification Search
CPC .... A61F 9/0026; A61F 9/0008; A61F 9/0017
USPC .......................... 351/246, 247, 204; 606/107
See application file for complete search history.

(56) References Cited

U.S. PATENT DOCUMENTS

| 5,089,022 | A | | 2/1992 | Koester et al. |
| 5,740,802 | A | | 4/1998 | Nafis et al. |
| 5,740,803 | A | | 4/1998 | Gray et al. |
| 5,757,461 | A | * | 5/1998 | Kasahara et al. ............. 351/206 |
| 5,867,210 | A | | 2/1999 | Rod |

(Continued)

FOREIGN PATENT DOCUMENTS

| RU | 2209053 C2 | 7/2003 |
| WO | WO 92/03989 | 3/1992 |

(Continued)

OTHER PUBLICATIONS

Arbelaez, et. al., "Clinical Outcomes of Corneal Vertex Versus Central Pupil References with Aberration-Free Ablation Strategies and LASIK," Dec. 2008, Investigative Ophthalmology & Visual Science, Dec. 2008, Lnkd-Pubmed: 18658090, vol. 49. NR. 12, pp. 5287-5294, XP002584895, ISSN: 1552-5783, Materials and Methods: p. 5287, Figure 5.

(Continued)

Primary Examiner — Zachary Wilkes
(74) Attorney, Agent, or Firm — Jason Finch

(57) ABSTRACT

A method for generating a radial alignment guide for an eye includes collecting preoperative alignment data relative to a pupil from an eye that is not dilated. The method also includes locating a pupil center of the eye while dilated. The method further includes displaying the alignment data on an image of the dilated eye relative to the pupil center. In particular embodiments, software embodied in a computer-readable medium is executable by a processor to perform the steps of such a method.

9 Claims, 4 Drawing Sheets

(56) References Cited

U.S. PATENT DOCUMENTS

| | | | |
|---|---|---|---|
| 5,975,084 | A | 11/1999 | Alpins |
| 6,241,356 | B1 | 6/2001 | Von Wallfeld et al. |
| 6,352,519 | B1 | 3/2002 | Anis et al. |
| 7,146,983 | B1 | 12/2006 | Hohla et al. |
| 7,331,667 | B2 * | 2/2008 | Grotehusmann et al. ...... 351/205 |
| 7,654,668 | B2 | 2/2010 | Neuhann et al. |
| 8,414,123 | B2 | 4/2013 | Boukhny et al. |
| 8,486,085 | B2 | 7/2013 | Moeller et al. |
| 2002/0097378 | A1 | 7/2002 | Saito et al. |
| 2003/0053025 | A1 | 3/2003 | Turner et al. |
| 2003/0060880 | A1 | 3/2003 | Feingold |
| 2003/0071893 | A1 | 4/2003 | Miller et al. |
| 2003/0120266 | A1 | 6/2003 | Fujieda |
| 2004/0100619 | A1 | 5/2004 | Olivier et al. |
| 2004/0102799 | A1 * | 5/2004 | Perez et al. ................... 606/166 |
| 2005/0025365 | A1 | 2/2005 | Oosawa |
| 2005/0117118 | A1 | 6/2005 | Miller et al. |
| 2005/0225721 | A1 | 10/2005 | Harris et al. |
| 2006/0247659 | A1 | 11/2006 | Moeller et al. |
| 2007/0055222 | A1 | 3/2007 | Hohla et al. |
| 2007/0274626 | A1 | 11/2007 | Sabeta |
| 2008/0247616 | A1 | 10/2008 | Pescatore et al. |
| 2009/0137988 | A1 * | 5/2009 | Kurtz ................................ 606/4 |

FOREIGN PATENT DOCUMENTS

| | | |
|---|---|---|
| WO | WO 01/28476 | 4/2001 |
| WO | 01/78584 A2 | 10/2001 |
| WO | 01/89373 A2 | 11/2001 |
| WO | 02/064031 A2 | 8/2002 |
| WO | WO 02/074248 | 9/2002 |
| WO | WO 03/022137 | 3/2003 |
| WO | 2006/044056 A2 | 4/2006 |
| WO | 2008/008044 A2 | 10/2008 |

OTHER PUBLICATIONS

Ma, et. al., "Simple Method for Accurate Alignment in Toric Phakic and Aphakic Intraocular Lens Implantation," Journal Cataract and Refractive Surgery, Surgery, Fairfax, VA Lnkd-DOI: 10.10163/J.JCRS.2008.04.041, vol. 34, No. 10, Oct. 1, 2008, pp. 1631-1636, XP025627296, ISSN: 0886-3350.

Nguyen, Et. al., "Digital Overlay Technique for Documenting Toric Intraocular Lens Axis Orientation," Oct. 2000, Journal of Cataract and Refractive Surgery, Oct. 2000, Lnkd-PubMed: 11033397, vol. 26, NR. 10, pp. 1496-1504, XP002584785, ISSN: 0886-3350.

Yang, et. al., "Pupil Location Under Mesopic, Photopic, and Pharmacologically Dilated Conditions," Investigative Ophthalmology & Visual Science, Association for Research in Vision and Ophthalmology, US, vol. 43, No. 7, Jul. 1, 2002, pp. 2508-2512, XP002537709, ISSN: 0146-0404, Pupil Center Location; p. 2509-2510, Discussion, p. 2511-2512.

International Search Report for International Application No. PCT/US2010/024482, 4 pages.

Written Opinion for International Application No. PCT/US2010/024482, 6 pages.

International Search Report for International Application No. PCT/US2010/024483, 4 pages.

Written Opinion for International Application No. PCT/US2010/024483, 5 pages.

European Search Report for Application No. 08162267.2. Publication No. EP2025305, Published Feb. 18, 2009, 3 pages.

Espacenet—Bibliographic data, English Abstract of RU2255716(C1), Avetisov, et al, "Method for Cataractous Extraction and Implantation of Intraocular Lens (IOL) at Correcting Initial Oblique Astigmatism"; Jul. 10, 2005; 1 pg.

Kent, "Locking on: Eye Tracking for the 21st Century", Rev. Ophthal., 2007, 7 pgs.

* cited by examiner

INTRAOCULAR LENS ALIGNMENT

RELATED APPLICATIONS

This application claims priority under 35 U.S.C. §119(e) to provisional application Ser. No. 61/153,709, filed Feb. 19, 2009, and provisional application Ser. No. 61/155,562, filed Feb. 26, 2009.

BACKGROUND

For the past decade, ophthalmic surgeons have tried several methods to correct preexisting astigmatism during cataract eye surgery, including making incisions into the cornea to alter the shape of the eye. Now due to the unique design of toric intraocular lenses (IOL), astigmatism can be reduced or corrected without further surgical intervention. A tonic IOL restores focus to the eye when the natural lens or cataract is removed, but it is also designed to correct preexisting astigmatism using the same technology that has been successfully used in contact lenses.

Before the surgery, the amount of corneal astigmatism that needs to be corrected must be determined. In general, the procedure is as follows:
1. Pre-Operative Examination (Keratometry, Corneal Topography, Slit Lamp)
2. Calculation of IOL orientation
3. IOL Selection
4. Surgical insertion of toric IOL and alignment according to pre-calculated axis The success of such procedures depends in part upon the angular accuracy of the IOL alignment. All of the above steps have the potential to introduce a certain degree of error resulting in under-correction of astigmatism. However, a dominant source of error is the misalignment of the toric IOL according to the calculated angular value after it is inserted into the anterior chamber of a patient's eye during the cataract procedure. This may be, for example, due to the fact that the calculated IOL angle is based on measurements conducted with the patient sitting upright (pre-op setup) and alert, while during surgery the patient is in the supine position where cyclorotation occurs and under the influence of local anesthetic. Each degree of angular error may cause a 3.3% loss of astigmatic correction by the toric IOL. Thus 10° of error may cause a 33% reduction in the effect of the toric IOL, which is equivalent to using a spherical lens without astigmatism correction.

In order to avoid error due to the cyclorotation effect, there are currently several techniques to mark the eye with the meridian and pre-calculated IOL axis of alignment during the pre-operative examination. These techniques typically require the surgeon to place reference marks at the 3-o'clock and 9-o'clock meridians at the limbus utilizing markers or puncturing devices. Markings made by markers may be inaccurate, and may wash away or drift. Furthermore, puncturing the cornea is invasive and carries considerable risk of infection and/or other side effects.

SUMMARY

In certain embodiments of the present invention, a method for generating a radial alignment guide for an eye includes collecting preoperative alignment data relative to a pupil from an eye that is not dilated. The method also includes locating a pupil center of the eye while dilated. The method further includes displaying the alignment data on an image of the dilated eye relative to the pupil center. In particular embodiments, software embodied in a computer-readable medium is executable by a processor to perform the steps of such a method.

In other embodiments, a system for generating a radial alignment guide for an eye includes a memory, a processor, and a display. The memory is operable to store preoperative alignment data relative to a pupil from an eye that is not dilated. The processor is operable to locate a pupil center of the eye while dilated. The display is operable to display the alignment data on an image of the dilated eye relative to the pupil center.

BRIEF DESCRIPTION OF THE DRAWINGS

The present invention may be understood with reference to the following drawings wherein.

DETAILED DESCRIPTION

In various embodiments of the present invention, toric intraocular lens alignment (IOL) for cataract surgery is improved by providing an accurate radial grid or alignment guide to assist a surgeon in lens placement. A slit lamp microscope may be used to obtain images of an eye, and an image overlay including a radial grid, lens alignment guide, and/or other fiducials for rotational alignment may be provided as a surgical guide in any suitable form including a computer display, a printed image of the eye showing information, or by direct projection onto the eye during the procedure According to various methods and systems described herein, a radial grid is centered on a center of the pupil and overlaid on an image of the eye (or in one embodiment directly onto the eye). The pupil center may be located, e.g., automatically using any appropriate center-finding image processing technique, or manually through a point-and-click computer interface or the like. For example, the pupil center can be located using a variety of image analysis techniques, including but not limited to the techniques described in U.S. Pat. No. 5,740,803 to Gray et al., which is incorporated herein by reference. The grid may include vertical and horizontal meridians and a scale at any suitable degree of accuracy. Within a user interface, angular measurements may be selected and marked on the grid to various features of the eye such as blood vessels, iris features, or any other appropriate fiducials. The grid may also include an alignment guide showing the correct rotational orientation for an IOL lens, as calculated prior to a surgical procedure. By calculating an angle relative to, e.g., the vertical meridian, an accurate guide may be displayed in the radial grid for use by a surgeon.

Figure 1:
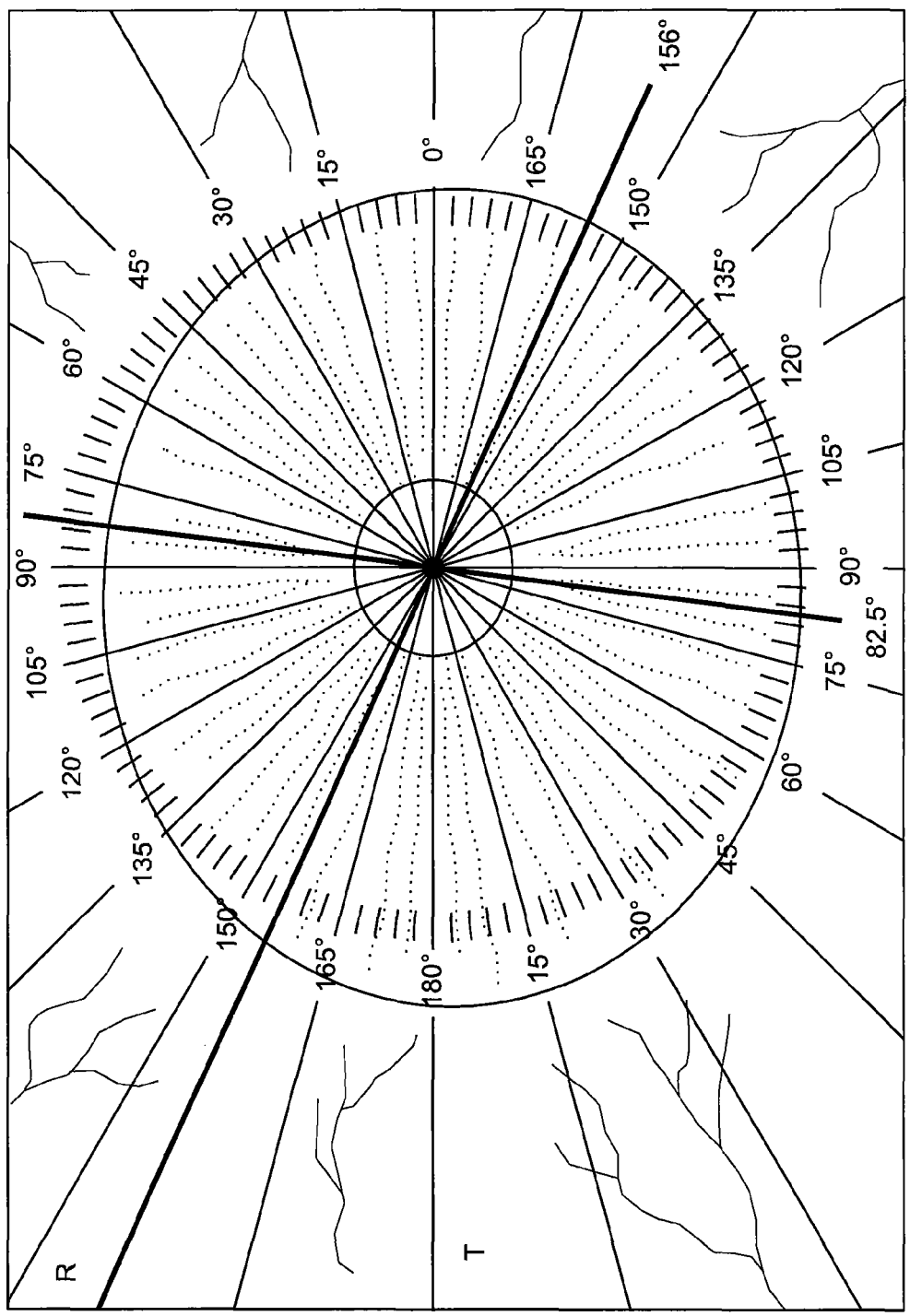
FIG. 1 shows an image of an eye with a radial overlay according to a particular embodiment of the present invention.

FIG. 1 shows an image of an eye with a radial overlay. As depicted, a horizontal meridian passes through 0 degrees and 180 degrees, and a vertical meridian passes through plus and minus 90 degrees. An angle of 82.5 degrees has been marked as a reference angle to some eye feature selected by a surgeon or the like, and an angle of 156 degrees is depicted for use in aligning a toric intraocular lens (also referred to generally herein as a lens.

Other aspects of systems and methods for aligning a lens are described below. In an embodiment using a slit lamp microscope, a suitable video camera may be mounted on a slit lamp microscope through a beam splitter. The camera may be connected to a computer with image acquisition hardware using a connector such as USB, FireWire or GigE port. Live display may be started, and the camera may be aligned so that the horizontal axis of the camera's field of view is aligned with the horizontal slit of the slit lamp. High quality images may be captured with the patient sitting upright, and software may attempt to automatically locate the central point of the pupil. The software may also include a manual pupil localization tool. Once the central point of the pupil is defined, the software may overlay a radial grid with its center located on that point as shown, e.g., in FIG. 1. The 0 to 180° axis of the radial will coincide with the 3- and 9-o'clock meridians of the eye since the camera is rotationally calibrated with the slit lamp. The software may also have the capability to provide the following:

Overlay of the toric IOL axis according to the angular value calculated through Keratometry. The toric axis IOL axis will cross the center of the dial and the angular value will be in reference to the 0 to 180° axis of the overlaid dial (see line with angle value 156 degrees in FIG. 1)

Overlay of axes that cross through the dial center and other anatomical landmarks that the surgeon chooses as fiducial marks on the eye's iris periphery or limbar vessels. The software will display the angular value next to each one of these reference points (see line with angle value 82.5 degrees in FIG. 1).

The software may also designate the images with the left or right eye designation and temporal or nasal side of the eye (see letters "R" and "T" in FIG. 1)

The processed images may be stored on the computer's hard drive, removable memory, or in the patient database of the medical facility. The surgeon may retrieve and display images with overlay in an operating room in a high quality photograph or on a monitor, or the overlay may be projected directly onto a patient's eye using an appropriate projector.

Figure 2:
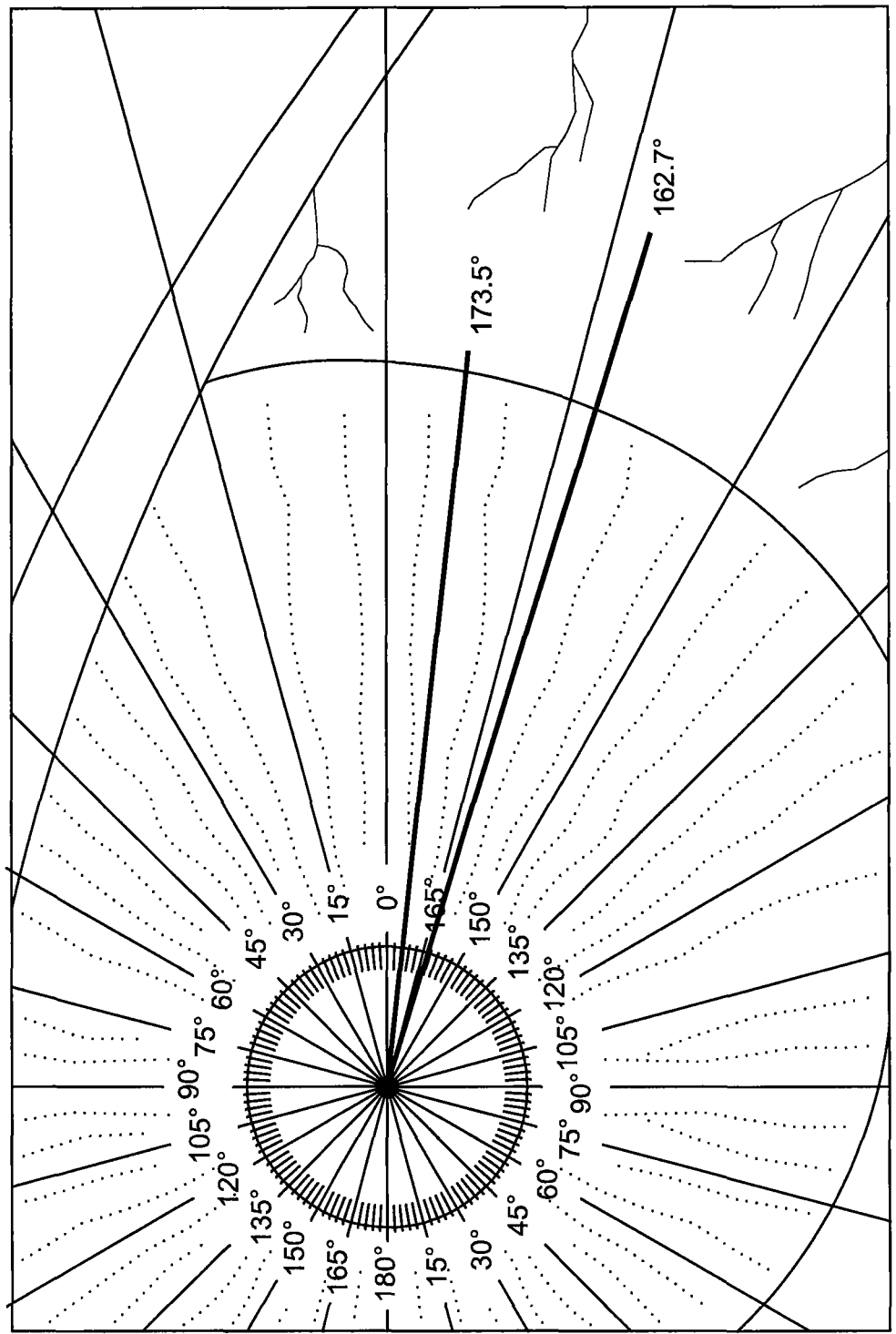
FIG. 2 shows an alternative configuration for a radial grid overlay, along with user-provided radial measurements, according to another embodiment of the present invention.
Figure 3:
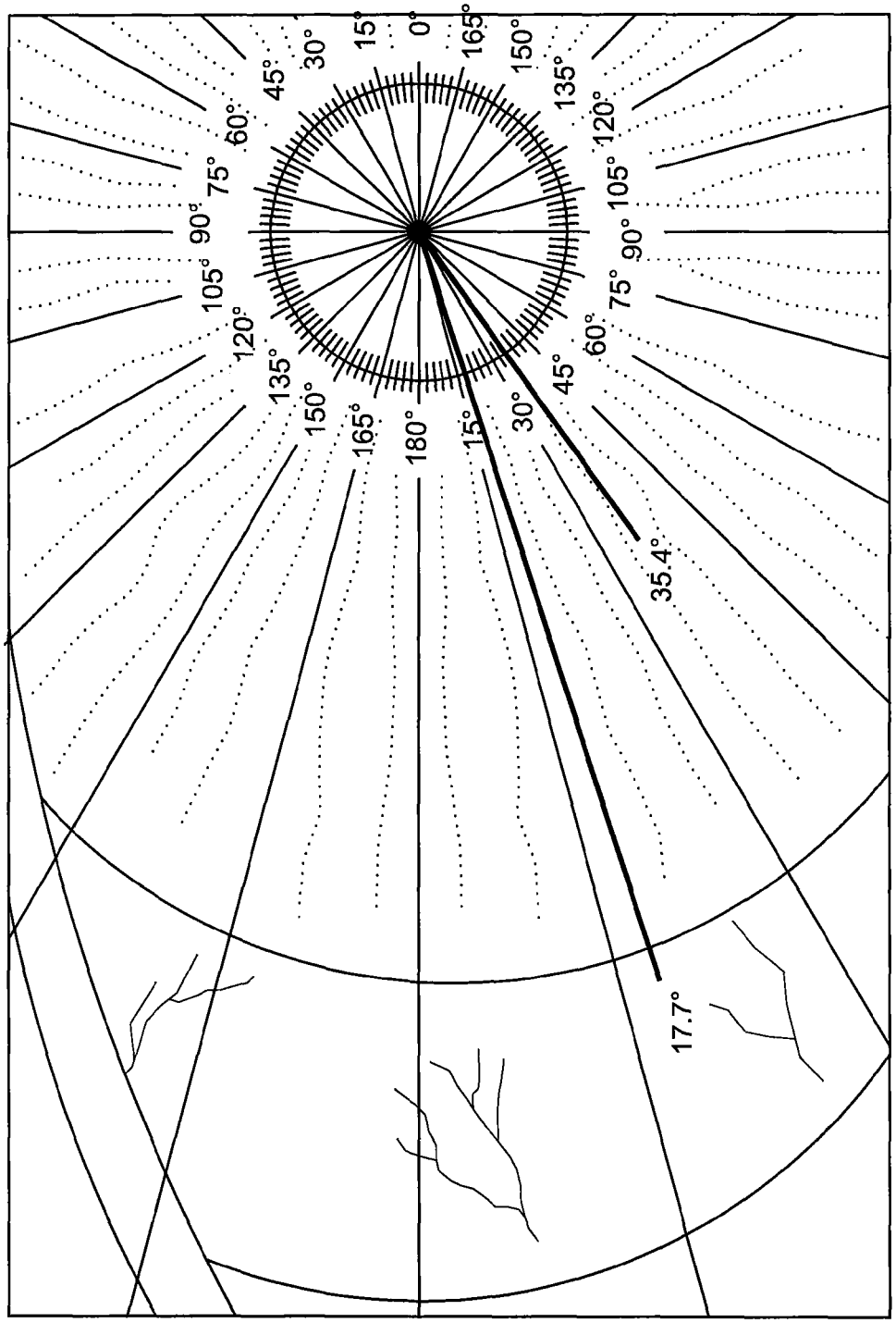
FIG. 3 shows an alternative configuration for a radial grid overlay, along with user-provided radial measurements according to another embodiment of the present invention.

Based on the overlaid axes of the fiducial points, the surgeon can accurately place a surgical protractor that determines toric IOL insertion regardless of the cyclorotation effect. As soon as the protractor is aligned with the actual eye meridians, the surgeon can proceed with aligning the toric IOL according to the calculated angular value. FIGS. 2 and 3 illustrate alternative arrangements for a radial overlay, along with user-provide measurements and/or lens alignment information.

Figure 4:
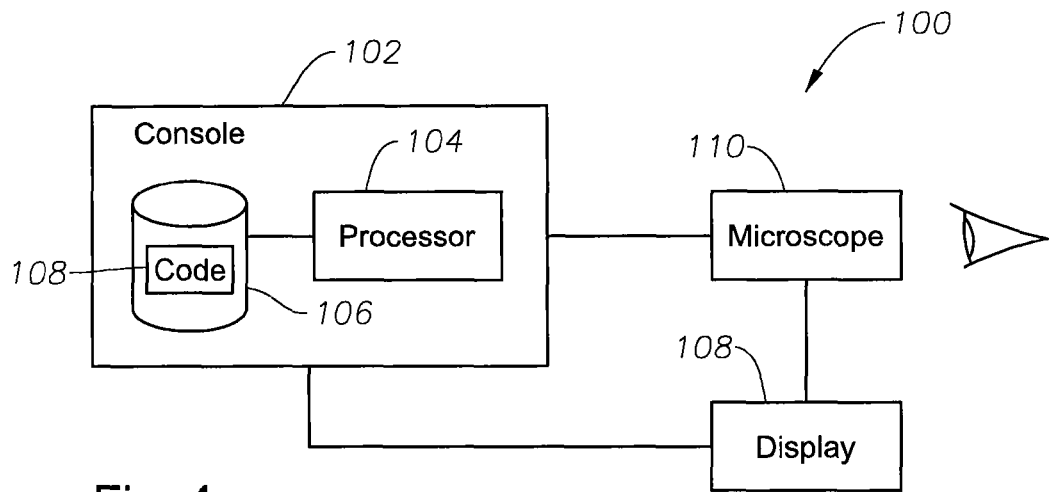
FIG. 4 is a block diagram of a surgical system according to a particular embodiment of the present invention.

This method addresses several sources of error in the IOL alignment process for cataract surgery by
a. Providing a mechanism for accurate camera alignment with the slit lamp microscope
b. Offering precise location of the pupil center based on image analysis
c. Enabling accurate protractor placement during surgery by guiding the surgeon to place the protractor according to the actual meridians of the eye hence generating an accurate reference angular system The methods or processes described above, and steps thereof, may be realized in hardware, software, or any combination of these suitable for a particular application. FIG. 4 is a block diagram of a system 100 for generating a surgical display according to a particular embodiment of the present invention. The system 100 includes a console 102 having a processor 104. The processor 104 may be one or more microprocessors, microcontrollers, embedded microcontrollers, programmable digital signal processors or other programmable device, along with internal and/or external memory 106. The processor 104 may also, or instead, be embodied in an application specific integrated circuit, a programmable gate array, programmable array logic, or any other device or combination of devices that may be configured to process electronic signals. The memory 106 may be any suitable form of data storage, including electronic, magnetic, or optical memory, whether volatile or non-volatile, that includes code 108 comprising instructions executed by processor 104. It will further be appreciated that computer executable code 108 may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

In the embodiment depicted in FIG. 4, the system 100 also includes a display 108 and a microscope 110 for observing an eye during surgery. The display 108 may include any suitable output device for generating an alignment guide for the eye, including a printer, a video display, or a light projector. In particular embodiments, the display 108 may be coupled to the microscope 110 so that the image is projected into the view of the microscope. The microscope 110 may be any suitable tool for visually inspecting the eye, which may include electronic and/or optical views. Various other suitable components, including any of the examples described herein, may also be substituted for the components of system 100.

Figure 5:
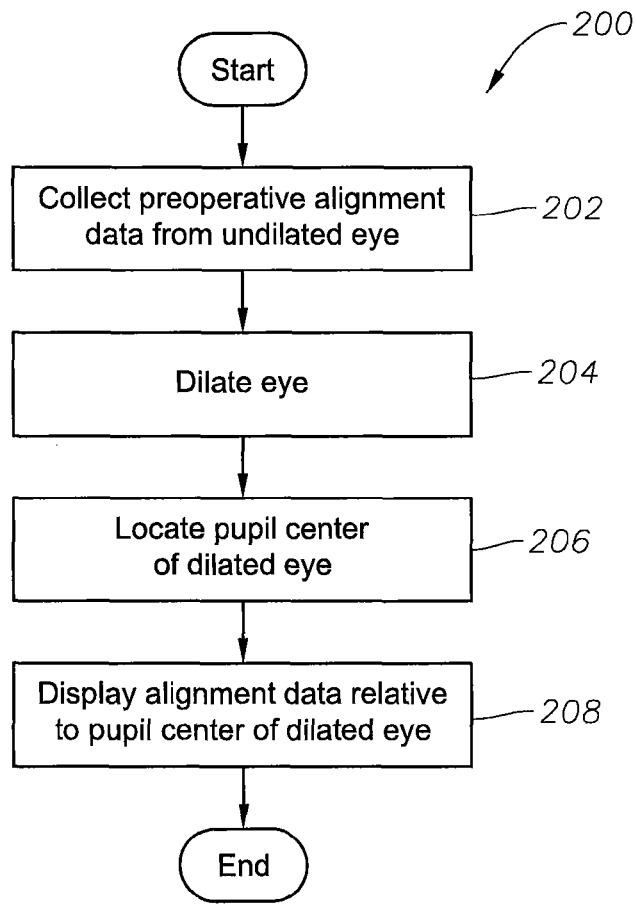
FIG. 5 is a flow chart illustrating an example method of generating a surgical display according to a particular embodiment of the present invention.

FIG. 5 is a flow chart 200 illustrating an example method for generating a surgical display including a radial alignment guide in accordance with a particular embodiment of the present invention. At step 202, preoperative alignment data relative to a pupil is collected from an eye that is not dilated. At step 204, the eye is dilated. At step 206, the pupil center is located. The pupil center can be located manually, such as by using a pointing device, or automatically, such as by image analysis software. At step 208, an alignment guide is displayed on an image of the dilated eye relative to the pupil center. The alignment guide can correspond to any of the various embodiments described herein.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art.

What is claimed is:

1. A method for generating a radial alignment guide for an eye, comprising:

collecting preoperative rotational alignment data relative to a pupil from an eye that is not dilated, the preoperative rotational alignment data comprising a rotational offset relative to a meridian of the eye;

locating a pupil center of the eye while dilated during implantation of a toric intraocular lens;

displaying a radial grid on an intraoperative image of the dilated eye, the radial grid comprising a vertical axis and a horizontal axis each passing through the located pupil center; and displaying a rotational alignment axis for the toric intraocular lens, during the implantation of the toric intraocular lens, on the intraoperative image of the dilated eye, the rotational alignment axis being offset relative to one of the vertical axis and the horizontal axis by an amount equal to the rotational offset of the preoperative rotational alignment data.

2. The method of claim 1, wherein locating the pupil center comprises manually moving a pointing device to locate a center of an eye.

3. The method of claim 1, wherein locating the pupil center comprises automatically locating the pupil center using image analysis software.

4. A system for generating a radial alignment guide for an eye, comprising:

a memory operable to store preoperative rotational alignment data relative to a pupil from an eye that is not dilated, the preoperative rotational alignment data comprising a rotational offset relative to a meridian of the eye;

a processor operable to locate a pupil center of the eye while dilated during implantation of a toric intraocular lens; and a display operable to display:

a radial grid on an intraoperative image of the dilated eye, the radial grid comprising a vertical axis and a horizontal axis each passing through the located pupil center; and a rotational alignment axis for the toric intraocular lens, during the implantation of the toric intraocular lens, on an intraoperative image of the dilated eye, the rotational alignment axis being offset relative to one of the vertical axis and the horizontal axis by an amount equal to the rotational offset of the preoperative rotational alignment data.

5. The system of claim 4, further comprising a pointing device that is manually movable to indicate a center of the pupil to the processor.

6. The system of claim 4, wherein the processor is operable to locate the pupil center using image analysis software.

7. Software embodied in a non-transitory computer-readable medium executable by a processor to perform the steps of:

collecting preoperative rotational alignment data relative to a pupil from an eye that is not dilated, the preoperative rotational alignment data comprising a rotational offset relative to a meridian of the eye;

locating a pupil center of the eye while dilated during implantation of a toric intraocular lens;

displaying a radial grid on an intraoperative image of the dilated eye, the radial grid comprising a vertical axis and a horizontal axis each passing through the located pupil center; and displaying a rotational alignment axis for the toric intraocular lens, during the implantation of the toric intraocular lens, on the intraoperative image of the dilated eye, the rotational alignment axis being offset relative to one of the vertical axis and the horizontal axis by an amount equal to the rotational offset of the preoperative rotational alignment data.

8. The software of claim 7, wherein locating the pupil center comprises receiving an indication of the center of the pupil from a pointing device.

9. The software of claim 7, wherein locating the pupil center comprises automatically locating the pupil center using image analysis software.

* * * * *